United States Patent
Joshi et al.

(10) Patent No.: US 8,388,578 B2
(45) Date of Patent: Mar. 5, 2013

(54) NON-ELECTRIC FLUID HEATING COMPONENT FOR USE WITH FLUID DISPENSER

(75) Inventors: Serena Joshi, San Francisco, CA (US); George N. Glavee, San Ramon, CA (US); Marshall S. Kriesel, St. Paul, MN (US)

(73) Assignee: BioQuiddity, Inc., San Francisco, CA (US)

( * ) Notice: Subject to any disclaimer, the term of this patent is extended or adjusted under 35 U.S.C. 154(b) by 626 days.

(21) Appl. No.: 12/587,472

(22) Filed: Oct. 6, 2009

(65) Prior Publication Data

US 2011/0082423 A1  Apr. 7, 2011

(51) Int. Cl.
*A61F 7/12* (2006.01)
*A61M 37/00* (2006.01)
*A61M 5/30* (2006.01)

(52) U.S. Cl. .............................. 604/113; 604/85; 604/70
(58) Field of Classification Search .................... 604/26, 604/113, 82–92, 181–143, 70
See application file for complete search history.

(56) References Cited

U.S. PATENT DOCUMENTS

2011/0082422 A1* 4/2011 Joshi et al. ................... 604/113

* cited by examiner

*Primary Examiner* — Nicholas Lucchesi
*Assistant Examiner* — Pritesh Patel
(74) *Attorney, Agent, or Firm* — James E. Brunton

(57) ABSTRACT

A non-electric heater apparatus for controllably heating and cooling fluid medicaments flowing from a medicament dispenser through the fluid delivery member of the apparatus by adding a suitable solution or solvent to a chemical component, such as magnesium chloride, or the like, to create an exothermic process that can be used to heat the fluid delivery member and the fluid flowing there through.

15 Claims, 7 Drawing Sheets

NON-ELECTRIC FLUID HEATING COMPONENT FOR USE WITH FLUID DISPENSER

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to non-electric fluid heating and cooling devices. More particularly, the invention concerns a novel, non-electric fluid heating and cooling device for use in connection with medicament dispensers for dispensing medicinal fluids to ambulatory patients.

2. Description of Related Art Including Information Disclosed Under 37 CFR 1.97 and 1.98

Many people die annually from hemorrhages. Treatment for severe hemorrhage usually requires the immediate and rapid infusion of critical fluids to prevent shock by replacing lost blood volume. To conduct this fluid resuscitation efficaciously in an austere environment, the medical professional must be able to easily transport the delivery system and fluid, and then initiate its use under significant logistical constraints. Furthermore, multi-step and time consuming methods for beginning fluid resuscitation can reduce a medical professional's ability to save lives in triage situations where a large number of patients are injured and in need of immediate medical attention.

In order to maximize the chance of survival, fluid resuscitation is often necessary where the casualty must replace the blood volume lost from the wound. Similarly, the use of IV fluids to restore intravascular volume is considered the best way to manage a severe burn casualty and replenish fluids lost in the first 24 hours. Furthermore, fluid warming is often needed to prevent the onset of hypothermia in trauma patients suffering from catastrophic hemorrhage, where military studies suggest the practice of warming IV fluids prior to administration has significantly decreased the rate of preventable deaths. Accidental or uncontrolled hypothermia is also a well-recognized problem among trauma patients, requiring immediate clinical intervention. Moreover, up to 60% of patients admitted to regional trauma centers can be hypothermic.

Although electronic portable fluid warming devices are currently available, they are not optimal for austere environments where weight and cube are of great concern. Current technologies typically rely on extremely heavy and bulky proprietary batteries, or electricity, that the medical professional must carry in addition to IV fluid bags, thereby eliminating space for other necessary medical supplies. Additionally, current technologies are not designed for direct integration to the IV fluid solution or delivery system modality. In other words, in addition to carrying the IV fluid bags, the medic must carry a separate fluid warming device and a separate battery; altogether which occupy more space and weight than the medic can afford. The invention described herein is a chemically driven fluid warming component/apparatus which would integrate in the dispenser or downstream of the dispenser on the administration line, without adding substantial weight or cube to the overall system. Because the technology relies on chemically generated heat, the need for electricity or proprietary batteries is eliminated, making it possible to heat fluids in austere environments, where previously warming IV fluids was very cumbersome.

Separate to electronic fluid warmers, other fluid warming "sleeves" or "hot packs" exist that can generate enough heat for an IV bag. Contrary to the fluid warming apparatus described herein, however, the sleeves and heat packs require several minutes to an hour to generate enough heat to warm the fluids to the necessary temperature. The length of time it takes to heat fluids with these warmers is insufficient in environments where the rapid delivery of fluids is required to prevent the casualty from hemorrhaging. Therefore, warming sleeves and hot packs also do not serve as ideal solutions in a trauma environment.

By way of additional background, administering intravenous fluids is a complex task that is even more difficult when intravenous volume IV replacement must be accomplished in the field. Very specific guidelines exist regarding appropriate physiological parameters that caregivers should use to identify which casualties actually require intravenous volume IV replacement in the field. Once intravenous or intra-osseous access is obtained and secured, current technology requires the caregiver to assemble the components of the IV solution prior to administration. A drip chamber must be connected to the fluid bag, the connecting line must be flushed, and then the line must be connected to the infusion site. When utilizing an intra-osseous site, the fluid bag then must be used in conjunction with a pressure infusing device to ensure appropriate flow rates. The complex logistical requirements for ordering, obtaining and storing appropriate medical supplies make the current technology most difficult. Further, the complexity of the process significantly jeopardizes safe and effective patient care within this environment.

As previously mentioned, in order to maximize the chance of survival, fluid resuscitation is often necessary where the casualty must replace the blood volume lost from the wound. Similarly, the use of IV fluids to restore intravascular volume is considered the best way to replenish fluids lost in the first 24 hours. In certain instances, fluid cooling, rather than fluid heating is needed to prevent IV fluids from reaching dangerously hot temperatures. Extremely hot IV fluids can cause tissue damage and hemolysis, a condition that is characterized by the breakdown of the red blood cell's membrane. Hot fluids can also be a disadvantage in treating heat-stroke casualties in the desert, or other high temperature environments. For example, the average daily temperatures in Iraq and Afghanistan can be in excess of 54° C. (130° F.) and temperatures exceeding 52.2° C. (126° F.) have been shown to damage tissue and blood cells. Although fluids can be stored at safe temperatures at higher level echelons of care, the medic in the austere environment (echelon 1) is at the mercy of the ambient temperature of the environment.

Although portable fluid cooling systems are currently available, they are not optimal for austere environments where weight, cube, and time required to cool are of great concern. Current electronic technologies are bulky, complex, and not suitable for austere environments due to weight and cube concerns. Alternatively, non-electric cooling pouches require the time consuming step of placing the IV fluid bag in the cooler and waiting 15 or more minutes; a step that is both time consuming and logistically complex as it requires the medic to carry both the IV fluid bag and the cooling pouch. The length of time it takes to cool fluids with these cooling systems is insufficient in environments where the rapid delivery of fluids is required to prevent the casualty from hemorrhaging.

The invention described herein is a chemically driven fluid cooling component/apparatus which would integrate in the dispenser or downstream of the dispenser on the administration line, without adding substantial weight or cube to the overall system. Because the technology relies on chemically generated cooling, the need for electricity or proprietary batteries is eliminated, making it possible to cool fluids in austere environments where, previously, cooling IV fluids was very cumbersome. This invention, with IV fluid dispenser and the integrated fluid cooling component as a self-contained unit, would have significant logistical benefits over the currently used and disparate flexible solution bag, fluid coolers, and heavy batteries.

BRIEF SUMMARY OF THE INVENTION

By way of brief summary, one form of the apparatus of the present invention comprises a non-electric heating and cooling means for interconnection with fluid dispensing devices of the character used to dispense medicaments to a patient. The apparatus of the invention includes a temperature altering chamber housing having an outer wall, a rear wall connected to the outer wall and a front cover connected to the outer wall, the front wall having a fluid inlet port to receive the medicinal fluids to be dispensed to a patient. The outer wall, the rear wall, and front cover cooperate to define an internal chamber having a fluid inlet. A fluid delivery member, which is contained within the internal chamber, has an outlet and an inlet in communication with the fluid inlet port of the front cover of the temperature altering chamber housing. A chemical component is contained within the internal chamber of the temperature altering chamber and an internally threaded container housing is connected to the temperature altering chamber housing. A collapsible container, which contains a solution or solvent that is to be intermixed with the chemical component, is carried within the internally threaded container housing and has an outlet in communication with the internal chamber of the temperature altering chamber housing. An externally threaded control member which has a pusher wall in engagement with the collapsible container is threadably connected to the internally threaded container housing for rotational movement relative thereto, to collapse the collapsible container and expel the solution therefrom.

With the forgoing in mind, it is an object of the present invention to provide a novel non-electric heating and cooling apparatus for controllably heating and cooling fluid medicaments flowing through the fluid delivery member of the apparatus by adding a suitable solution to a chemical component to create either an exothermic or endothermic process that can be used to selectively heat or cool the fluid delivery member and the fluid flowing there through.

Another object of the invention is to provide a novel dispensing apparatus as described in the preceding paragraphs in which the fluid delivery member comprises an inner length of helix shaped tubing and an outer length of helix shaped tubing that circumscribes the inner length of helix shaped tubing.

Another object of the invention is to provide an apparatus of the class described which is compact and lightweight, is easy to use and is extremely reliable in operation.

Another object of the invention is to provide an apparatus that is easy and inexpensive to manufacture in large quantities.

DETAILED DESCRIPTION OF THE INVENTION

Definitions—As used herein the following terms mean:
Collapsible
  To cause to fold, break down, or fall down or inward or as in bent-over or doubled-up so that one part lies on another.

Collapsible Container

A dispensing apparatus in which one or more walls of the container are made of a material which will deform (collapse) when pressure is applied thereto; or a dispensing apparatus having a collapsible or telescoping wall structure.

Exothermic/Endothermic

Exothermic is characterized by, or formed with, evolution of heat, as, an exothermic reaction; as opposed to endothermic which is characterized by or formed with absorption of heat.

Figures 3, 4, 5, 6, 7, 7A, 7B, 7C, 8:
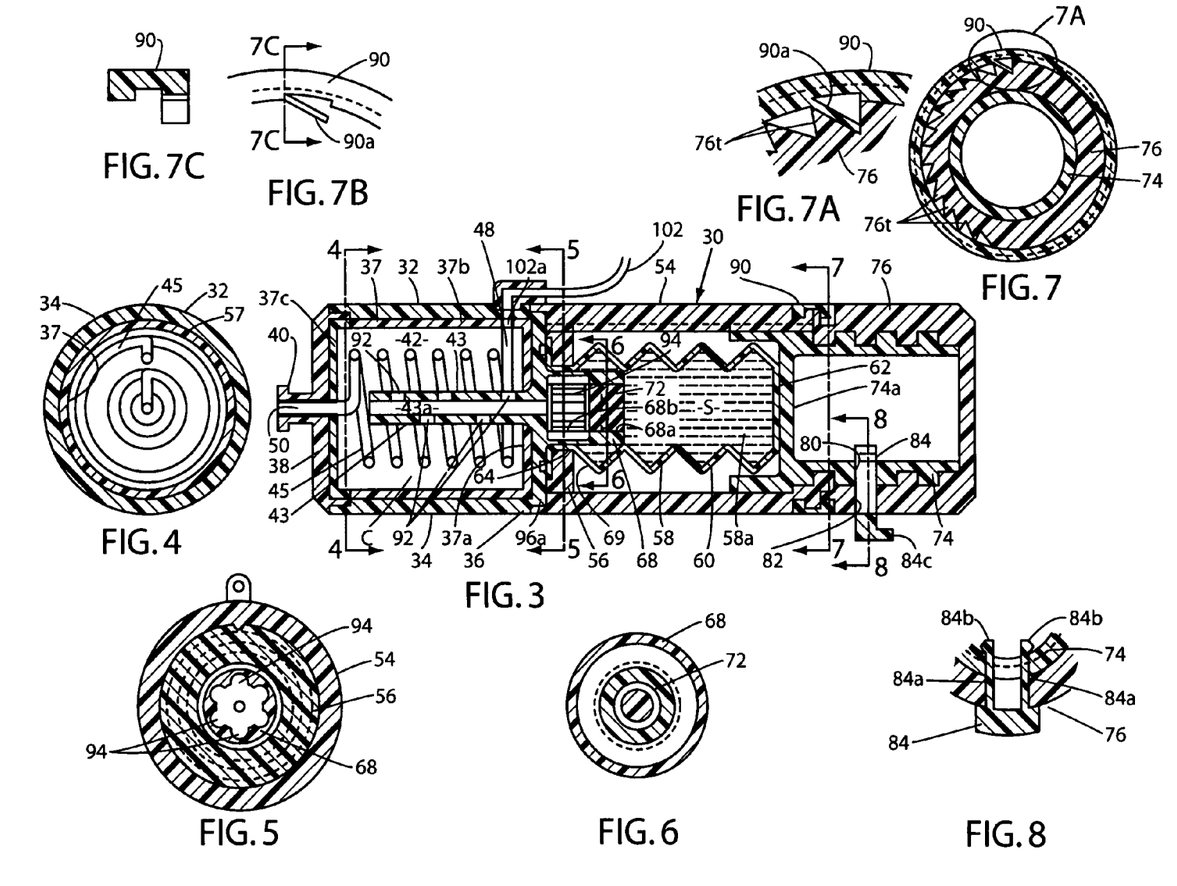
FIG. 3 is a longitudinal cross-sectional view of the device shown in FIG. 1 of the drawings.
FIG. 4 is a cross-sectional view taken along lines 4-4 of FIG. 3.
FIG. 5 is a cross-sectional view taken along lines 5-5 of FIG. 3.
FIG. 6 is a cross-sectional view taken along lines 6-6 of FIG. 3.
FIG. 7 is a cross-sectional view taken along lines 7-7 of FIG. 3.
FIG. 7A is a greatly enlarged cross-sectional view of the area designated in FIG. 7 as "7A".
FIG. 7B is a greatly enlarged fragmentary view of a portion of the anti-rotation collar of the device.
FIG. 7C is a cross-sectional view taken along lines 7C-7C of FIG. 7B.
FIG. 8 is a cross-sectional view taken along lines 8-8 of FIG. 3.

Referring to the drawings and particularly to FIGS. 1 through 9, one form of the non-electric heating apparatus of the invention for controllably heating and cooling medicaments to be dispensed to a patient is there shown and generally designated by the numeral 30. The apparatus of this form of the invention comprises a heating-cooling, or temperature altering chamber housing 32 that includes an outer wall 34, a rear portion 36 (FIG. 3) and a front cover 38 connected to outer wall 34. Disposed within chamber housing 32, is an insulation barrier generally designated by the numeral 37, the purpose of which will presently be described. Front cover 38 has a fluid inlet port 40 for receiving the medicinal fluids to be dispensed to a patient. Inlet port 40 is here provided in the form of a conventional male Luer connector. As best seen in FIG. 3, outer wall 34, rear portion 36 and front cover 38 cooperate to define an internal chamber 42 having a fluid inlet 44.

Extending forwardly of the rear wall 37a of the insulation barrier 37 is an elongated dispersing tube 43, the purpose of which will presently be described. Contained within internal chamber 42 of chamber housing 32 is the previously mentioned insulation barrier 37 which, in addition to rear wall 37a, comprises a sidewall 37b and a front wall 37c (FIG. 3). Insulation barrier 37 is constructed from an appropriate insulating material that effectively insulates chamber housing 32 from internal chamber 42.

Also housed within internal chamber 42 is the important fluid delivery member of the apparatus, which here comprises a generally helically shaped tube 45 that circumscribes the elongated dispersing tube 43 in the manner shown in FIG. 3 of the drawings. Helically shaped tube 45 is provided with an outlet 48 and an inlet 50 that is in communication with the fluid inlet port 40 of front cover 38.

For a purpose presently to be described, a chemical component, generally designated in FIG. 3 as "C" is contained within the internal chamber 42 of chamber housing 32. With respect to the exothermic process and by way of non-limiting example, in one form of the invention the chemical component "C" comprises aluminum oxide. In another form of the invention, the chemical component "C" comprises copper oxide. However it is to be understood that the chemical component "C" is a solid that can be selected from a group consisting of cement mixture, silicon elastomers, polybutadiene rubbers, bisphenol-A, aluminum oxide, iron oxide, aluminum, copper, copper oxide, phosphoric acid, iron, calcium and other alkali earth metals, potassium and other alkali metals, strontium oxide and other metal oxides, sodium hydroxides and other metal hydroxides, and anhydrous solid salts (e.g. calcium chloride, magnesium chloride, iron chloride, zinc sulfate, copper sulfate, iron sulfate, sodium sulfate, barium iodide and calcium iodate).

With respect to the endothermic process for cooling the fluid to be delivered to the patient, while the cooling of fluid may, in principle, be achieved through any endothermic process, examples of suitable endothermic chemical processes include the following:

1. Reaction of ammonium salts with water as for example:

$NH_4NO_{3(s)} + H_2O_{(l)} \rightarrow HNO_{3(aq)} + NH_{3(aq)}$ $NH_4Cl_{(s)} + H_2O_{(l)} \rightarrow HCl_{(aq)} + NH3_{(aq)}$ $NH_4IO_{3(s)} + H_2O_{(l)} \rightarrow HIO_{3(aq)} + NH_{3(aq)}$ 2. Reaction of ammonium salts with base as for example:

$NH_4Cl_{(s)} + Ba(OH)_2.8H_2O_{(s)} + H_2O_{(l)} \rightarrow BaCl_2.2H_2O_{(aq)} + H_2O_{(l)}$ $NH_4SCN_{(s)} + Ba(OH)_2.8H_2O_{(s)} + H_2O_{(l)} \rightarrow BaSCN_2.2H_2O_{(aq)} + NH3_{(aq)} + H_2O_{(l)}$ 3. Reaction of Sodium Bicarbonate with water as for example:

$NaHCO_{3(s)} + H_2O_{(l)} \rightarrow NaOH_{(aq)} + CO_{2(g)}$

4. Reaction of Sodium carbonate with acids as for example:

$NaHCO_{3(s)} + H_3PO_{4(aq)} \rightarrow Na_3PO_{4(aq)} + CO_{2(g)}$ $NaHCO_{3(s)} + CH_3COOH_{(aq)} \rightarrow NaCH_3COO_{(aq)} + CO_{2(g)}$ $3NaHCO_{3(s)} + H_3C_6CO_{7(aq)} \rightarrow Na_3C_6CO_{7(aq)} + 3CO_{2(g)} + 3H_2O_{(l)}$ 5. Dissolution of potassium salts as for example:

$KNO_{3(s)} + H_2O_{(l)} \rightarrow KNO_{3(aq)}$ $KIO_{3(s)} + H_2O_{(l)} \rightarrow KIO_{3(aq)}$ $K_4Fe(CN)_{6(s)} + H_2O_{(l)} \rightarrow K_4Fe(CN)_{6(aq)}$ 6. Evaporation of innocuous volatile solvents as for example:

Water→Water vapor $Acetone_{(l)} \rightarrow Acetone_{(g)}$ $Pentane_{(l)} \rightarrow Pentane_{(g)}$ $Fluorochlorocarbon_{(l)} \rightarrow Fluorochlorocarbon_{(g)}$

Referring once again to FIG. 3 of the drawings, connected to chamber housing 32 is a container housing 54 that houses an annular shaped retainer member 56. Also housed within container housing 54 is a collapsible container 58 having a generally bellows shaped side wall 60, an end wall 62 and a cylindrically shaped neck portion 64 that is received within annular shaped retainer member 56 in the manner shown in FIG. 3. As illustrated in FIG. 3, collapsible container 58 has an outlet 66 that is in communication with internal chamber 42 of the heating chamber housing 32 via dispersion tube 43.

Figures 1, 2:
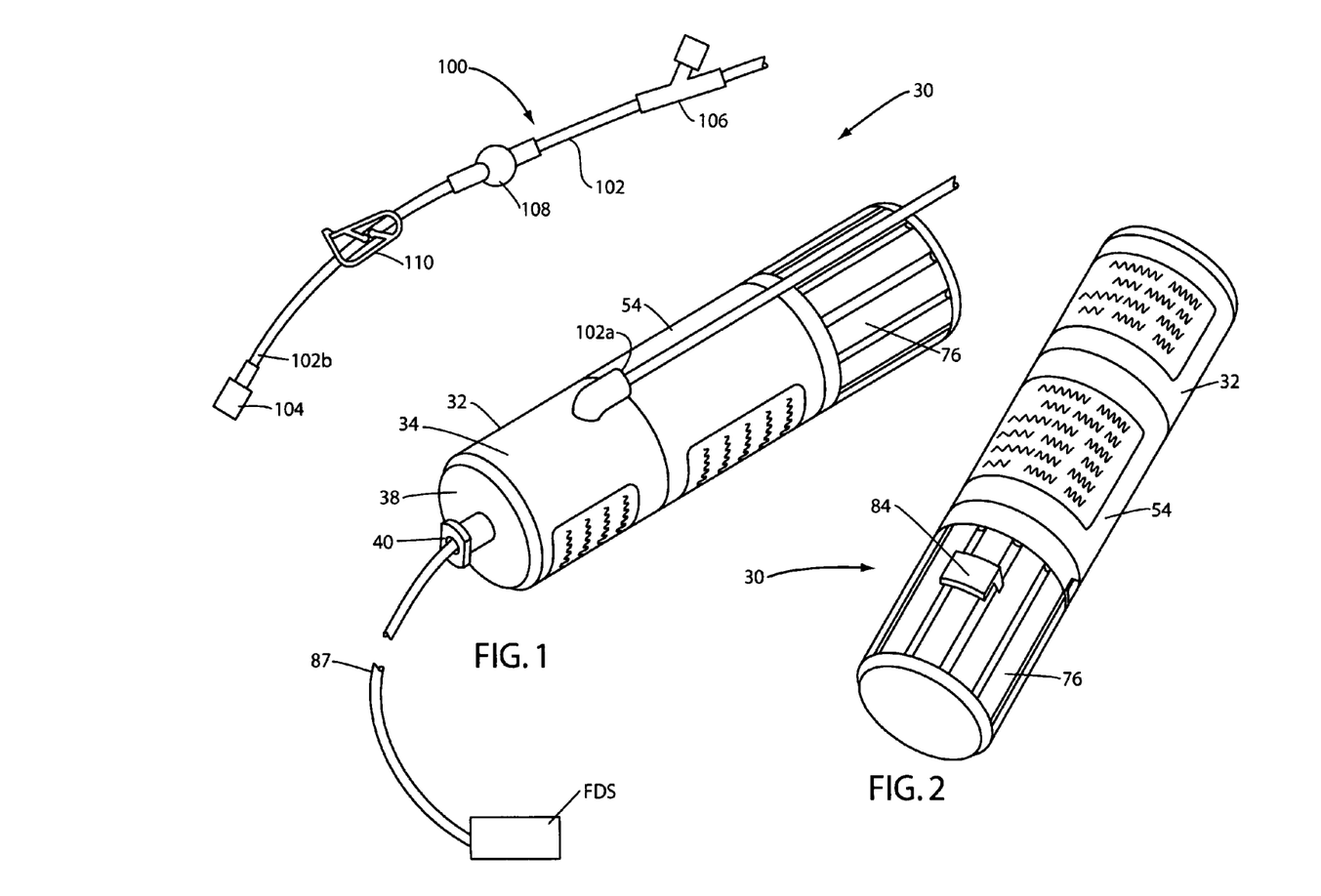
FIG. 1 is a generally perspective front view of one form of the non-electric fluid heating and cooling device for use in connection with medicament dispensers for dispensing medicinal fluids to ambulatory patients.
FIG. 2 is a generally perspective rear view of the device shown in FIG. 1.

Contained within the reservoir 58a of the collapsible container 58 is a solution or solvent generally designated as "S". In a manner presently to be described, the chemical component "C" that is contained within the internal chamber 42 of chamber housing 32 is controllably intermixed with the solution or solvent "S" to cause either an exothermic or an endothermic reaction that provides the source for heating or cooling the fluid received from the fluid delivery source "FDS" (FIG. 1). By way of non-limiting example, in one form of the present form of the invention, the solution or solvent "S" comprises water that is controllably inter-mixed with a selected chemical component to create either an exothermic reaction or an endothermic reaction. Where the chemical "C" comprises magnesium oxide the following exothermic reaction occurs:

$MgCl_{2(s)} + 6H_2O_{(l)} \rightarrow MgCl_2.6H_2O_{(s)} \Delta H = -150\ kJ/mol.$ In another form of the invention, the solution "S" comprises aqueous phosphoric acid that is controllably inter-mixed with the chemical component strontium oxide to create the following exothermic reaction:

$2H_3PO_{4(aq)} + 3SrO_{(s)} \rightarrow Sr_3(PO_4)_{2(s)} + 3H_2O_{(l)}$ $\Delta H = -704$ kJ/mol.

However, it is to be understood that in creating the exothermic process, the solution or solvent "S" can be selected from the group consisting of water, styrene, epichlorohydrin, vinegar, ascorbic acids, oxalic acid, aqueous solutions of strong acids, aqueous sodium hydroxide and other metal hydroxides, and solutions or blends of polymerization initiator in the polymerization processes.

Other desirable exothermic processes created by mixing the chemical component "C" that is contained within the internal chamber 42 of the heat chamber housing 32, with the solution or solvent "S" contained within the collapsible container 58, include the following:

$Ba(OH)_{2(s)} + 8H_2O_{(l)} \rightarrow Ba(OH)_2 \cdot 8H_2O_{(s)}$ $\Delta H = -126$ kJ/mol $SrO_{2(s)} + 8H_2O_{(l)} \rightarrow SrO_2 \cdot 8H_2O_{(s)}$ $\Delta H = -117$ kJ/mol $3Sr(OH)_{2(aq)} + 2H_3PO_{4(s)} \rightarrow Sr_3PO_{4(2(aq))} + 6H_2O$ $\Delta H = -223$ kJ/mol $Ca_{(s)} + 2H_2O_{(l)} \rightarrow Ca(OH)_{2(aq)} + H_2$ $\Delta H = -432$ kJ/mol With regard to the forgoing reactions, the hydration reactions are attractive because both products and reactants are environmentally friendly. The acid base reactions are desirable because of the amount of energy and the end products produced. The Ca/water reaction produces a significant amount of energy and is desirable where a substantial amount of energy is required.

With respect to the endothermic process for cooling the fluid to be delivered to the patient, while the cooling of fluid may, in principle, be achieved through any endothermic process, examples of suitable endothermic chemical processes include the following:

1. Reaction of ammonium salts with water as for example:

$NH_4NO_{3(s)} + H_2O_{(l)} \rightarrow HNO_{3(aq)} + NH_{3(aq)}$ $NH_4Cl_{(s)} + H_2O_{(l)} \rightarrow HCl_{(aq)} + NH3_{(aq)}$ $NH_4IO_{3(s)} + H_2O_{(l)} \rightarrow HIO_{3(aq)} + NH_{3(aq)}$ 2. Reaction of ammonium salts with base as for example:

$NH_4Cl_{(s)} + Ba(OH)_2 \cdot 8H_2O_{(s)} + H_2O_{(l)} \rightarrow BaCl_2 \cdot 2H_2O_{(aq)} + NH3_{(aq)} + H_2O_{(l)}$ $NH_4SCN_{(s)} + Ba(OH)_2 \cdot 8H_2O_{(s)} + H_2O_{(l)} \rightarrow BaSCN_2 \cdot 2H_2O_{(aq)} + NH3_{(aq)} + H_2O_{(l)}$ 3. Reaction of Sodium Bicarbonate with water as for example:

$NaHCO_{3(s)} + H_2O_{(l)} \rightarrow NaOH_{(aq)} + CO_{2(g)}$

Figure 3A:
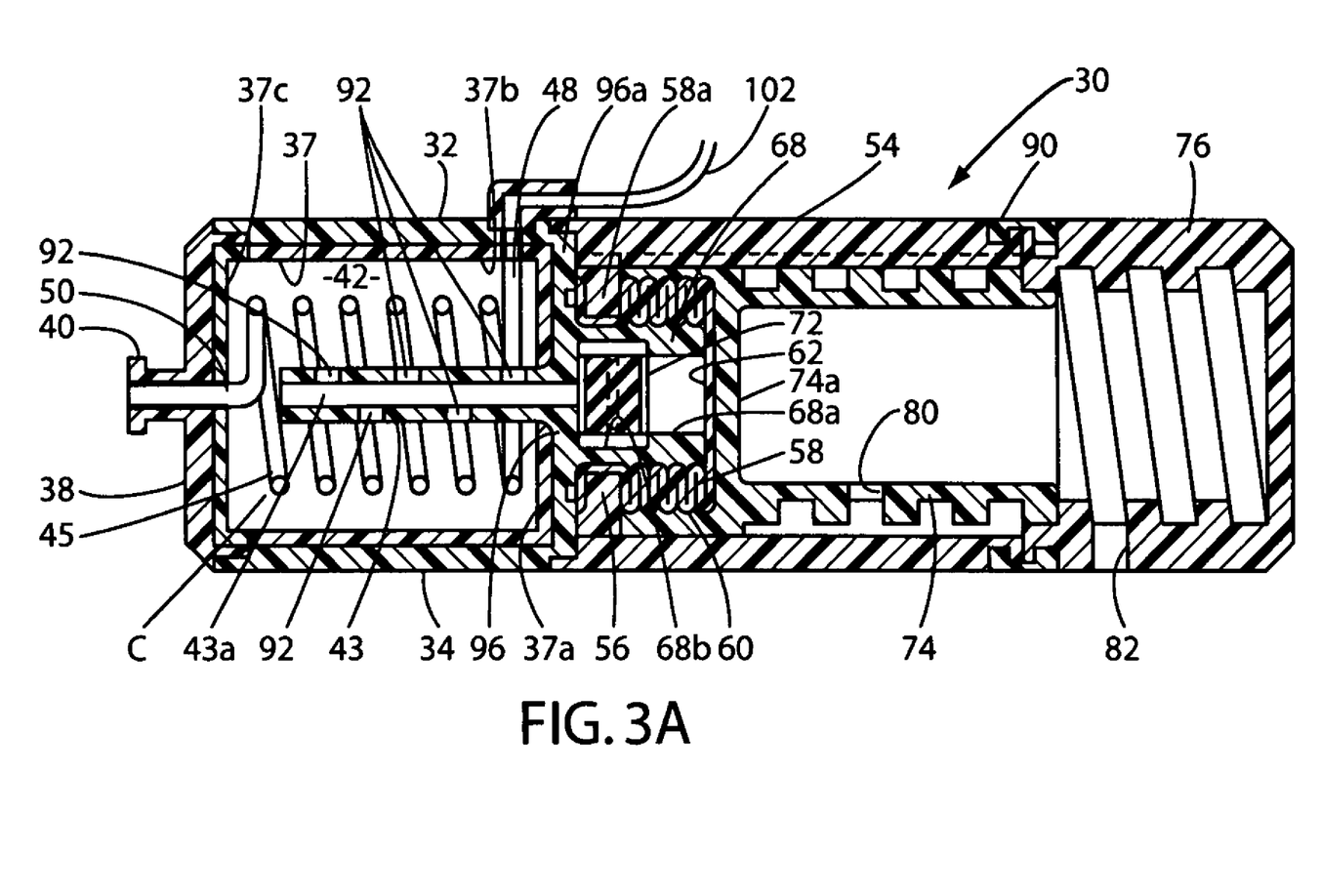
FIG. 3A is a cross-sectional view similar to FIG. 3, illustrating the appearance of the device following the collapse of the collapsible container of the apparatus.

4. Reaction of Sodium carbonate with acids as for example:

$NaHCO_{3(s)} + H_3PO_{4(aq)} \rightarrow Na_3PO_{4(aq)} + CO_{2(g)}$ $NaHCO_{3(s)} + CH_3COOH_{(aq)} \rightarrow NaCH_3COO_{(aq)} + CO_{2(g)}$ $3NaHCO_{3(s)} + H_3C_6CO_{7(aq)} \rightarrow Na_3C_6CO_{7(aq)} + 3CO_{2(g)} + 3H_2O_{(l)}$ 5. Dissolution of potassium salts as for example:

$KNO_{3(s)} + H_2O_{(l)} \rightarrow KNO_{3(aq)}$ $KIO_{3(s)} + H_2O_{(l)} \rightarrow KIO_{3(aq)}$ $K_4Fe(CN)_{6(s)} + H_2O_{(l)} \rightarrow K_4Fe(CN)_{6(aq)}$ 6. Evaporation of innocuous volatile solvents as for example:

Water→Water vapor $Acetone_{(l)} \rightarrow Acetone_{(g)}$ $Pentane_{(l)} \rightarrow Pentane_{(g)}$ $Fluorochlorocarbon_{(l)} \rightarrow Fluorochlorocarbon_{(g)}$ Carried within the neck portion 64 of the collapsible container 58 is a seal plug housing 68 that includes reduced diameter portion 68a and an enlarged diameter portion 68b. Disposed within the reduced diameter portion of the seal plug housing is a seal plug 72. Seal plug 72 is movable within the seal plug housing between a first retracted position shown in FIG. 3 and a second advanced position wherein it is located within the enlarged diameter portion 68b as shown in FIG. 3A of the drawings. The purpose of seal plug 72 will presently be described.

Forming an important feature of the apparatus of the present invention is an externally threaded pusher member 74 that includes a pusher wall 74a that is in engagement with end wall 62 of the collapsible container (see FIG. 3). Threadably connected to externally threaded pusher member 74 is an internally threaded control member 76 that is adapted for rotational movement relative to the pusher member so as to move the pusher member from the first retracted position shown in FIG. 3 to the second advanced position shown in FIG. 3A to collapse the collapsible container and expel the solution or solvent "S" therefrom.

In order to prevent inadvertent rotational movement between the externally threaded control member and the internally threaded container housing, locking means are provided. In this regard, as best seen in FIGS. 3 and 8, pusher member 74 is here provided with a radial bore 80 and control member 76 is provided with an aligned radial bore 82. With this construction, the locking means here comprises a locking pin 84 that is removably carried within the radial bores of the pusher member and the control member. As best seen in FIG. 8 of the drawings, locking pin 84 is provided with spaced apart legs 84a that terminate in gripping protuberances 84b that releasably grip the inner surface of the pusher member. As indicated in FIG. 3 of the drawings, the lower extremity of pin 84 is provided with an outwardly extending gripping tab 84c that is spaced apart from the outer surface of the control knob so that the caregiver can insert a fingernail into the space in a manner to readily extract the locking pin from the assembly.

Figure 9:
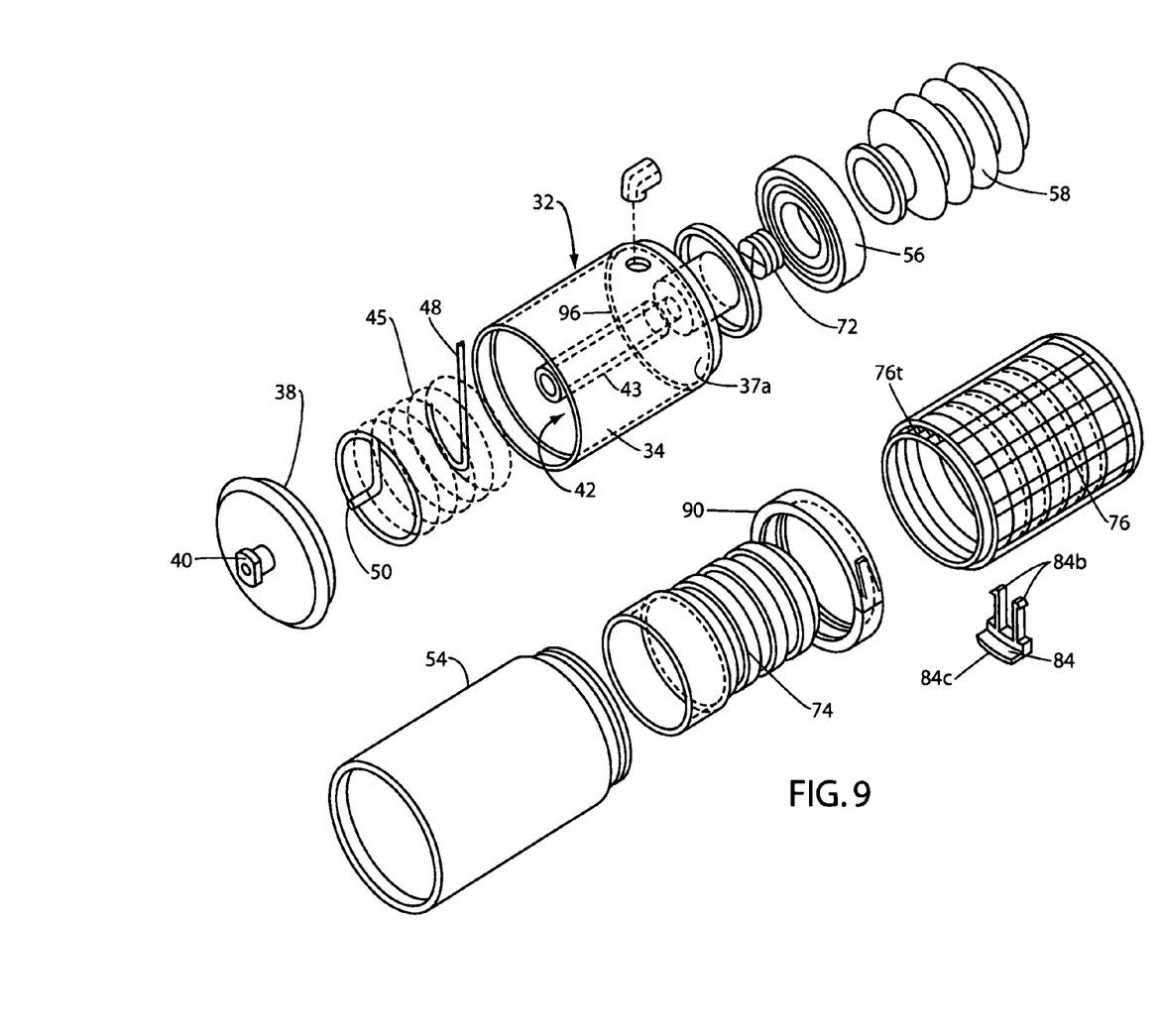
FIG. 9 is a generally perspective, exploded view of the device shown in FIGS. 1, 2 and 3 of the drawings.

In using the apparatus of the invention, the first step is to inter-connect the fluid delivery system FDS with inlet 40 of the cover 38 via line 87 (FIG. 1) to establish communication between the fluid delivery system and internal chamber 42 of temperature altering chamber housing 32. This done, the locking pin 84 is removed from the aligned radial bores 80 and 82 in the manner previously described, to permit control member 76 to be irreversibly, threadably advanced relative to the internally threaded pusher member 74 from the first retracted position shown in FIG. 3 of the drawings to the second advanced position shown in FIG. 3A of the drawings. In order to prevent rotational movement of the externally threaded control member in a reverse direction, in an attempt to return the pusher member to its first retracted position, anti-rotation means are provided. This novel anti-rotation means here comprises a uniquely configured collar 90 that is mounted over the forward, reduced diameter portion 54 of container housing 54 (FIG. 9).

Figure 7D:
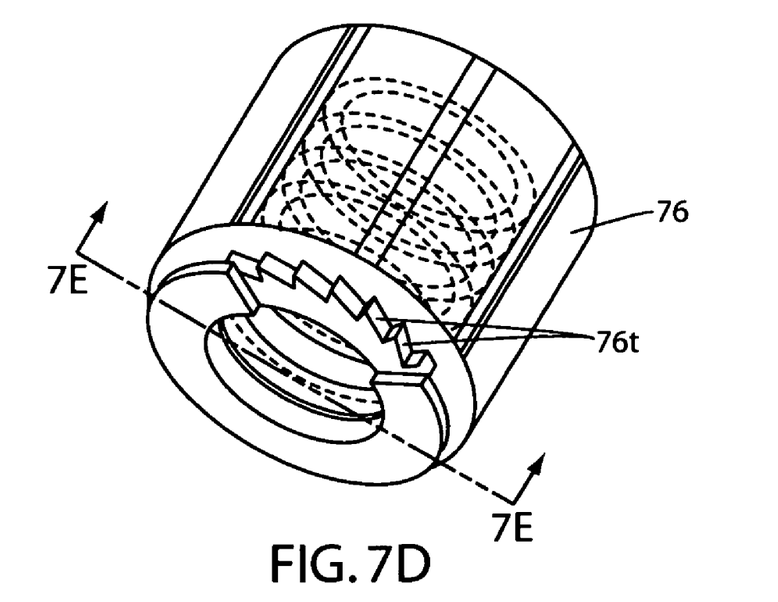
FIG. 7D is a generally perspective view of a portion of the threaded control member and anti-rotation collar of the device.
Figure 7E:
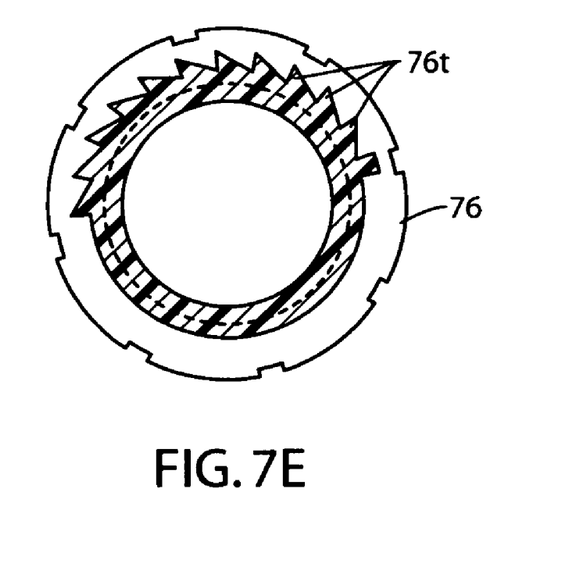
FIG. 7E is a view taken along lines 7E-7E of FIG. 7D.

Referring to FIGS. 7B, 7C, 7D, 7E and 9, it can be seen that the inner periphery of collar 90 is provided with an inwardly extending, resiliently deformable locking tab 90a (FIG. 7A). As the control member is rotated relative to the pusher member, the locking tab 90a will engage a plurality of circumferentially spaced, yieldably deformable saw-toothed locking teeth 76t provided on the periphery of the control member (FIGS. 7, 7D and 7E). While the locking tab 90a will readily slide over the locking teeth 76t so as to permit advancement of the control member to the position shown in FIG. 3A of the drawings, its configuration is such that it will engage the locking teeth in a manner to positively prevent counter rotation of the control knob, thereby preventing the control member from returning to its first starting position.

As the control knob is advanced to the position shown in FIG. 3A, the collapsible container 58 will be collapsed and the solution or solvent "S" contained there within will be forced through the fluid passageways, or grooves 94, formed in the enlarged diameter portion 68b of the seal plug housing 68 (FIG. 5). From the fluid passageways 94, the fluid will flow into dispersion tube 43 and then into chamber 42 of chamber housing 32 via the plurality of longitudinally spaced fluid outlet passageways 92 that communicate with internal chamber 42. As the solution or solvent "S" enters chamber 42 it will intermix with the chemical component "C" to form a selected one of the previously mentioned exothermic or endothermic solutions that function to controllably heat or cool the fluid delivery member, or helix tube 45. As the bellows sidewall 60 of the collapsible container 58 collapses, the solution or solvent "S" will force the seal plug 72 to move within the seal plug housing between a first retracted position shown in FIG. 3 and a second advanced position wherein it is located within the enlarged diameter portion 68b as shown in FIG. 3A. As indicated in FIG. 3 of the drawings, dispersing tube 43 comprises a part of the dispersion assembly 96 of the invention, which also includes a flange portion 96a. When the seal plug 72 is in its advanced position shown in FIG. 3A, it sealably engages flange 96a, thereby preventing reverse flow of the solution toward the now collapsed collapsible container 58 via the central passageway 43a of the dispersion tube.

The exothermic or endothermic solution formed within chamber 42 functions to controllably heat or cool the helical tube 45 as well as the fluid to be delivered to the patient which, upon heating or cooling of the helical tube 45, can be delivered to the helical tube from the fluid delivery system FDS that is interconnected with a helical tube in the manner shown in FIG. 1 of the drawings. In the case of the formation of an exothermic solution, as the fluid from the fluid delivery system flows through, the helical tube 45 is preferably heated to body temperature, or to a temperature slightly greater than body temperature.

As illustrated in FIGS. 3 and 3A of the drawings, a conventional administration set 100 is interconnected with the helical tube 45. More particularly, as best seen in FIG. 1 of the drawings, the administration set includes an administration line 102 having a first end 102a that is connected to the outlet 48 of the helix tube 45 and a second end 102b that is connected to a conventional Luer connector 104. Connected intermediate the first and second ends of the administration line is a conventional injector Y site 106, a conventional gas vent 108, and a conventional line clamp 110.

After the fluid flowing through the helix tube 45 is either heated or cooled, it will flow through outlet 48 of the helix tube and into the inlet of the administration for delivery to the patient in a conventional manner.

Referring now to FIGS. 10 through 16 of the drawings, an alternate form of the non-electric heating or cooling apparatus of the invention for controllably heating or cooling medicaments to be dispensed to a patient is there shown and generally designated by the numeral 110. The apparatus of this latest form of the invention is similar in most respects to that shown in FIGS. 1 through 10 and like numbers are used in FIGS. 10 through 16 to identify like components. The primary difference between this latest form of the invention and that earlier described resides in the provision of a differently configured fluid delivery member 112. More particularly, fluid delivery member 112, which is housed within the temperature altering chamber housing 32, here comprises an inner helically shaped tube 114 that circumscribes the elongated dispersing tube 43 and an outer helically shaped tube 116 that circumscribes inner helical shaped tube 114.

Figures 10, 11, 12, 13, 13A, 14, 15:
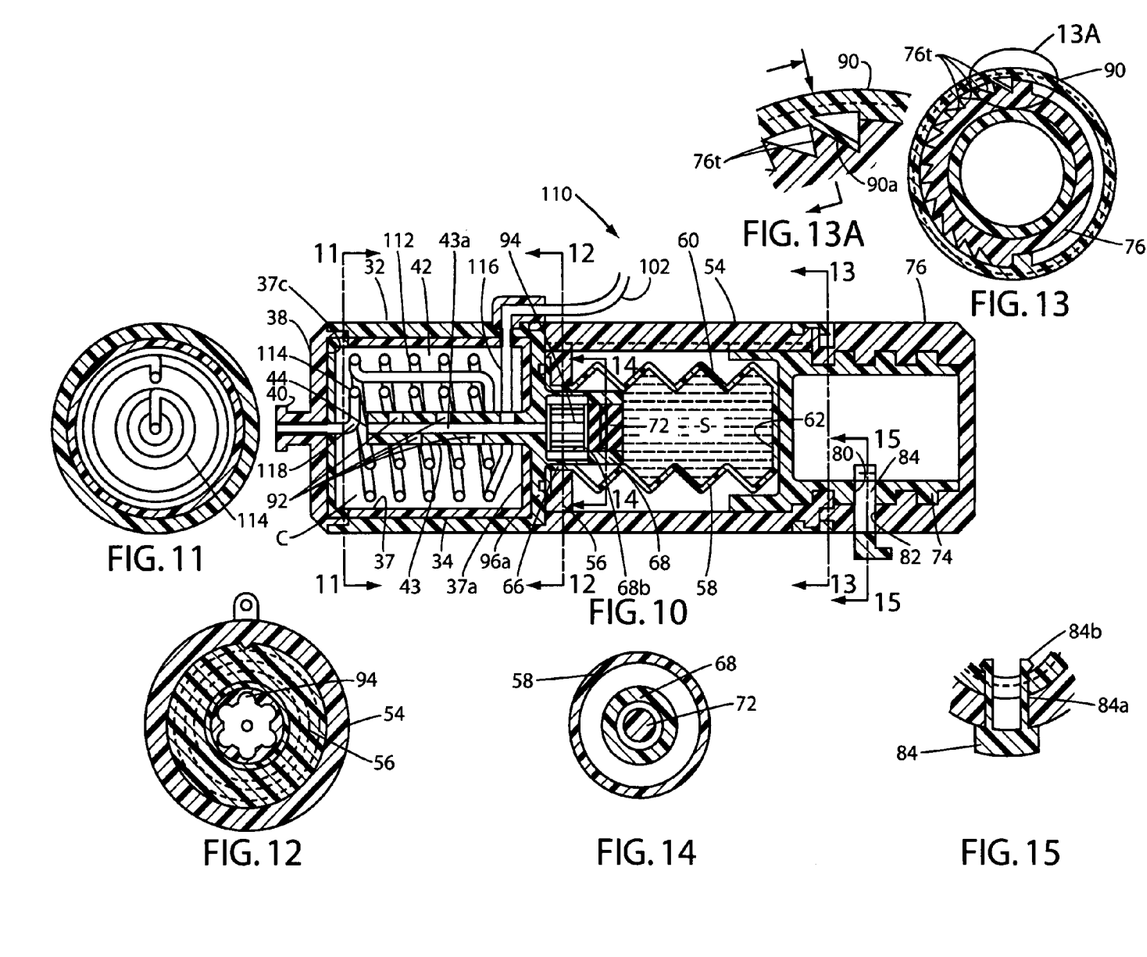
FIG. 10 is a longitudinal cross-sectional view of an alternate form of the non-electric fluid heating and cooling device for use in connection with medicament dispensers for dispensing medicinal fluids to ambulatory patients.
FIG. 11 is a cross-sectional view taken along lines 11-11 of FIG. 10.
FIG. 12 is a cross-sectional view taken along lines 12-12 of FIG. 10.
FIG. 13 is a cross-sectional view taken along lines 13-13 of FIG. 10.
FIG. 13A is an enlarged fragmentary view of the area designated as 13A-13A in FIG. 13.
FIG. 14 is a cross-sectional view taken along lines 14-14 of FIG. 10.
FIG. 15 is a cross-sectional view taken along lines 15-15 of FIG. 10.

As before, apparatus 110 comprises a temperature altering chamber housing 32 that includes an outer wall 34 and a front cover 38 connected to outer wall 34. Like the earlier described embodiment, an insulation barrier 37 which is of substantially identical construction to that previously described, is disposed within chamber housing 32. Front cover 38 has a fluid inlet port 40 for receiving the medicinal fluids to be dispensed to a patient. As best seen in FIG. 10, outer wall 34 and front cover 38 cooperate to define an internal chamber 42 having a fluid inlet 44. Extending forwardly of the rear wall 37a of the insulation barrier 37 is the previously mentioned dispersing tube 43. As best seen in FIG. 10, helically shaped tube 114 of fluid delivery member 112 is provided with an outlet 116 and an inlet 118 that is in communication with the fluid inlet port 40 of front cover 38.

Disposed within internal chamber 42 of the temperature altering chamber housing 32 is a chemical component, generally designated in FIG. 10 as "C". Chemical component "C" is substantially identical to that previously described and, as before, is controllably intermixed with a solution or solvent "S" contained within the reservoir of a collapsible container 58 to cause either an exothermic reaction or an endothermic reaction that provides the source of heat for heating or cooling the fluid received from the fluid delivery source "FDS" (FIG. 1).

Connected to chamber housing 32 in the manner shown in FIG. 10 of the drawings is a container housing 54 that houses an annular shaped retainer member 56. Also housed within container housing 54, is a collapsible container 58 which is substantially identical in construction and operation to that previously described. Contained within the reservoir of the collapsible container is the solution or solvent "S" that is substantially identical to that previously described and, in the manner previously described, is controllably intermixed with the component "C" to cause either an exothermic or endothermic process. As illustrated in FIG. 10, collapsible container 58 has an outlet 66 that is in communication with internal chamber 42 of the heating chamber housing 32 via dispersion tube 43.

Figure 16:
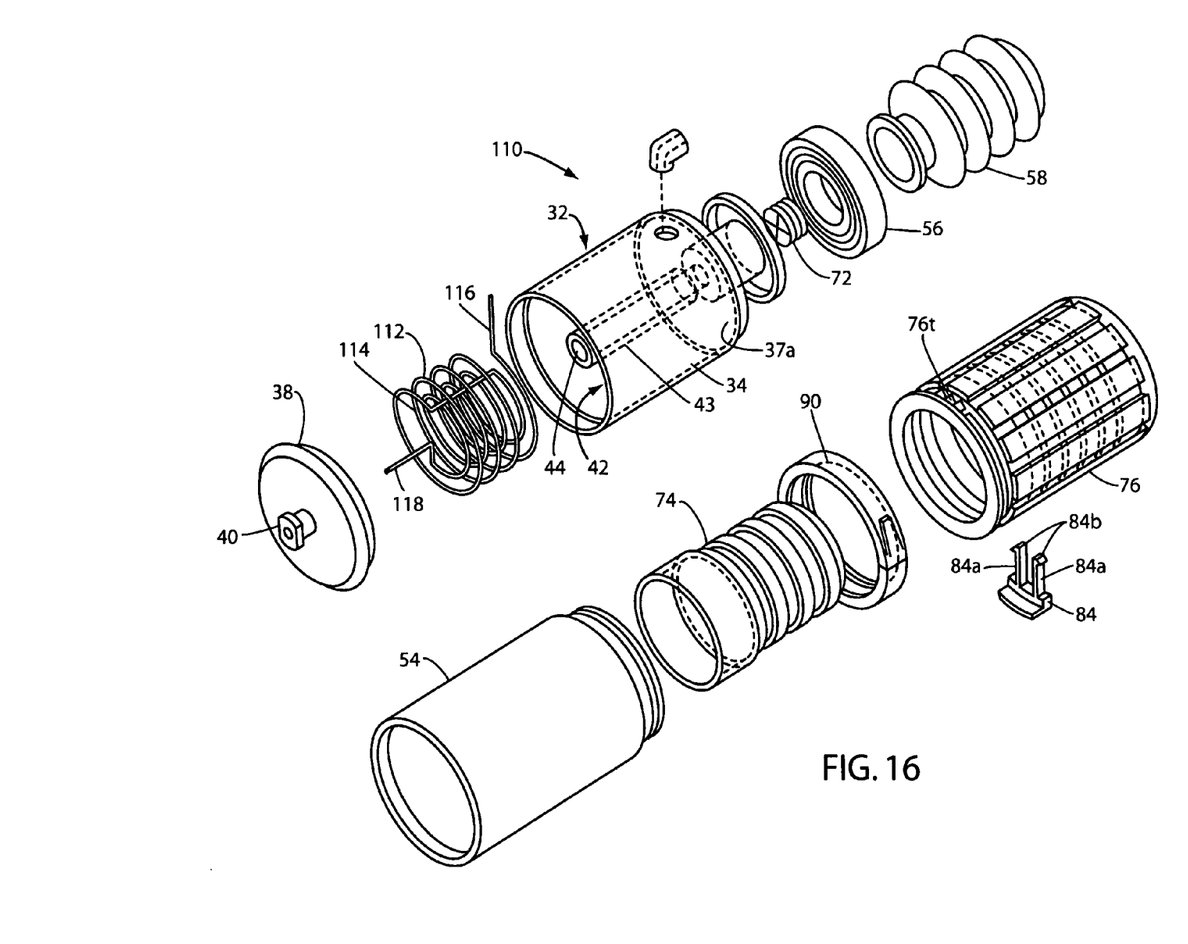
FIG. 16 is a generally perspective, exploded view of the alternate form of the device shown in FIG. 10 of the drawings.

The apparatus of this latest form of the invention includes an externally threaded pusher member 74 that is also substantially identical in construction and operation to that previously described (see FIGS. 10 and 16).

Threadably connected to externally threaded pusher member 74 is an internally threaded control member 76 that is adapted for rotational movement relative to the pusher member so as to move the pusher member from the first retracted position shown in FIG. 10 to a second advanced position to collapse the collapsible container and expel the solution or solvent "S" therefrom. Internally threaded control member 76 is also substantially identical in construction and operation to that previously described.

In order to prevent inadvertent rotational movement between the externally threaded control member and the internally threaded container, housing locking means of the character previously described are provided (see FIGS. 10 and 15). Similarly, in order to prevent rotational movement of the externally threaded control member in a reverse direction in an attempt to return the pusher member to its first retracted position, anti-rotation means of the character previously described are provided (see FIGS. 10, 13 and 13A).

In using the apparatus of the invention, the first step is to inter-connect the fluid delivery system FDS with inlet 40 of the cover 38 via line 87 (FIG. 1) to establish communication between the fluid delivery system and internal chamber 42 of chamber housing 32. This done, the locking pin 84 is removed from the aligned radial bores 80 and 82 in the manner previously described to permit control member 76 to be irreversibly, threadably advanced, relative to the internally threaded pusher member 74, from the first retracted position shown in FIG. 3 of the drawings to the second advanced position.

As the control knob is advanced to the advanced position, the collapsible container 58 will be collapsed and the solution or solvent "S" contained there within will be forced through the fluid passageways, or grooves 94, formed in the enlarged diameter portion 68b of the seal plug housing 68 (FIG. 12). From the fluid passageways 94, the fluid will flow into dispersion tube 43 and then into chamber 42 of the temperature altering chamber housing 32 via the plurality of longitudinally spaced fluid outlet passageways 92 that communicate with internal chamber 42. As the solution or solvent "S" enters chamber 42, it will intermix with the chemical component "C" to form a selected one of the previously mentioned exothermic or endothermic solutions that function to controllably heat or cool the fluid delivery member, or double helix tube 112. As before, as the bellows sidewall 60 of the collapsible container 58 collapses, the solution or solvent "S" will force the seal plug 72 to move within the seal plug housing between a first retracted position shown in FIG. 10 and a second advanced position wherein it is located within the enlarged diameter portion 68b, as shown in FIG. 3A. As indicated in FIG. 3 of the drawings, dispersing tube 43 comprises a part of the dispersion assembly 96 of the invention which also includes a flange portion 96a. When the seal plug 72 is in its advanced position it sealably engages flange 96a, thereby preventing reverse flow of the solution toward the now collapsed collapsible container 58 via the central passageway 43a of the dispersion tube.

The solution formed within chamber 42 functions to controllably heat or cool the double helical tube 112, as well as the fluid to be delivered to the patient, which upon heating or cooling of the double helical tube 112, can be delivered to the helical tube from the fluid delivery system FDS that is inter-connected with a helical tube in the manner shown in FIG. 1 of the drawings.

As before, a conventional administration set 100 is inter-connected with the double helical tube 112, in the manner illustrated in the drawings. After the fluid flowing through the double helix tube 112 is either heated or cooled, it will flow through outlet 123 of the outer helix tube 116 and into the inlet of the administration set for delivery to the patient in a conventional manner.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for altering the temperature of medicinal fluids to be dispensed to a patient comprising:
   (a) a temperature altering chamber housing having a fluid inlet port and an internal chamber;
   (b) a fluid delivery member contained within said internal chamber of said temperature altering chamber housing, said fluid delivery member having an outlet and an inlet in communication with said fluid inlet port of said temperature altering chamber housing;
   (c) a chemical component contained within said internal chamber of said temperature altering chamber;
   (d) a container housing connected to said temperature altering chamber housing;
   (e) a collapsible container carried within said container housing, said collapsible container having an outlet in communication with said internal chamber of said temperature altering chamber housing;
   (f) a solution contained within said collapsible container;
   (g) an externally threaded pusher member connected to said container housing for movement between a first retracted position and a second advanced position, said pusher member having a pusher wall in engagement with said collapsible container; and
   (h) an internally threaded control member threadably connected to said externally threaded pusher member for rotational movement relative thereto to urge said pusher member from said first retracted position toward said second advanced position;
   (i) a collapsible container that includes a cylindrically shaped neck portion and in which said apparatus further comprises:
   (j) an elongated dispersing tube connected to and extending from said rear wall of said heating chamber, said dispersing tube being in communication with said collapsible container;
   (k) an annular shaped retainer member carried within said internally threaded container housing for receiving said cylindrically shaped neck portion of said collapsible container;
   (l) a seal plug housing disposed within said cylindrically shaped neck portion of said collapsible container, said seal plug housing having a reduced diameter portion and an enlarged diameter portion having a plurality of circumferentially spaced bypass flow channels in communication with said internal chamber; and
   (m) a seal plug carried within said reduced diameter portion of said seal plug housing for movement between a first retracted position and a second advanced position within said enlarged diameter portion.

2. The apparatus as defined in claim 1 further including locking means carried by said internally threaded container housing for preventing rotational movement between said externally threaded control member and said internally threaded container housing.

3. The apparatus as defined in claim 1 further including anti-rotation means carried by said internally threaded container housing for preventing rotational movement of said externally threaded control member from said second advanced position toward said first retracted position.

4. The apparatus as defined in claim 1 further including an administration set interconnected with said outlet of said fluid delivery member.

5. The apparatus as defined in claim 1 in which said fluid delivery member comprises a helically shaped tube circumscribing said elongated dispersing tube.

6. The apparatus as defined in claim 1 in which said fluid delivery member comprises an inner helically shaped tube circumscribing said elongated dispersing tube and an outer helically shaped tube circumscribing said inner helically shaped tube.

7. An apparatus for heating medicinal fluids to be dispensed to a patient comprising:
(a) a temperature altering chamber housing including an outer wall, a rear wall connected to said outer wall and a front cover connected to said outer wall, said front cover having a fluid inlet port to receive the medicinal fluids to be dispensed to a patient, said outer wall, said rear wall and said front cover cooperating to define an internal chamber having a fluid inlet;
(b) an elongated dispersing tube connected to and extending from said rear wall of said temperature altering chamber housing and into said internal chamber of said temperature altering chamber housing;
(c) a fluid delivery member contained within said internal chamber of said temperature altering chamber housing, said fluid delivery member comprising a helically shaped tube circumscribing said elongated dispersing tube and having an outlet and an inlet in communication with said fluid inlet port of said front cover of said heat chamber housing;
(d) a chemical component contained within said internal chamber of said temperature altering chamber housing;
(e) an internally threaded container housing connected to said temperature altering chamber housing;
(f) a collapsible container carried within said internally threaded container housing, said collapsible container having an outlet in communication with said internal chamber of said heat chamber housing;
(g) a solution contained within said collapsible container for intermixing with said chemical component contained within said internal chamber of said temperature altering chamber housing; and
(h) an externally threaded control member having a pusher wall in engagement with said collapsible container, said externally threaded control member being threadably connected to said internally threaded container housing for rotational movement relative thereto between a first retracted position and a second advanced position to collapse said collapsible container;
wherein a collapsible container includes a cylindrically shaped neck portion and in which said apparatus further comprises:
(i) an annular shaped retainer member carried within said internally threaded container housing for receiving said cylindrically shaped neck portion of said collapsible container;
(j) a seal plug housing disposed within said cylindrically shaped neck portion of said collapsible container, said seal plug housing having a reduced diameter portion and an enlarged diameter portion having a plurality of circumferentially spaced bypass flow channels in communication with said fluid inlet of said internal chamber; and
(k) a seal plug carried within said reduced diameter portion of said seal plug housing for movement between a first retracted position and a second advanced position within said enlarged diameter portion.

8. The apparatus as defined in claim 7 further including locking means carried by said internally threaded container housing for preventing rotational movement between said externally threaded control member and said internally threaded container housing.

9. The apparatus as defined in claim 7 further including anti-rotation means carried by said container housing for preventing rotational movement of said externally threaded control member in a manner to move said pusher member from said second advanced position toward said first retracted position.

10. The apparatus as defined in claim 7 further including an administration set interconnected with said outlet of said fluid delivery member.

11. The apparatus as defined in claim 9 in which said fluid delivery member comprises an inner helically shaped tube circumscribing said elongated dispersing tube and an outer helically shaped tube circumscribing said inner helical shaped tube.

12. An apparatus for altering the temperature of medicinal fluids to be dispensed to a patient comprising:
(a) a temperature altering chamber housing including a generally cylindrical outer wall, a rear wall connected to said outer wall and a front cover connected to said outer wall, said front cover having a fluid inlet port in the form of a male Luer connector to receive the medicinal fluids to be dispensed to a patient, said outer wall, said rear wall and said front cover cooperating to define an internal chamber having a fluid inlet;
(b) an elongated dispersing tube connected to and extending from said rear wall of said temperature altering chamber housing;
(c) a fluid delivery member contained within said internal chamber of said temperature altering chamber housing, said fluid delivery member comprising a helically shaped tube circumscribing said elongated dispersing tube, said helically shaped tube having an outlet and an inlet in communication with said fluid inlet port of said front cover of said temperature altering chamber housing;
(d) a chemical component contained within said internal chamber of said temperature altering chamber housing;
(e) a generally cylindrical container housing connected to said temperature altering chamber housing;
(f) an annular shaped retainer member carried within said container housing;
(g) a collapsible container carried within said container housing, said collapsible container having a bellows side wall, an end wall connected to said bellows side wall and a cylindrically shaped neck portion connected to bellows side wall, said cylindrically shaped neck portion being received within said annular shaped retainer member and having an outlet in communication with said elongated dispersing tube;
(h) a seal plug housing disposed within said cylindrically shaped neck portion of said collapsible container, said seal plug housing having a reduced diameter portion and an enlarged diameter portion having a plurality of circumferentially spaced bypass flow channels in communication with said elongated dispersing tube;
(i) a seal plug carried within said reduced diameter portion of said seal plug housing for movement between a first retracted position and a second advanced position within said enlarged diameter portion;
(j) a solution contained within said collapsible container for mixing with said chemical component contained within said internal chamber of said temperature altering chamber housing;

(k) an externally threaded pusher member having a pusher wall in engagement with said collapsible container, said externally threaded pusher member being moveable relative to said container member between a first retracted position and a second advanced position to collapse said collapsible container;

(l) an internally threaded generally cylindrical control member threadably connected to said externally threaded pusher member for rotational movement relative thereto to move said pusher member from said first retracted position toward said second advanced position;

(m) locking means carried by said externally threaded control member for preventing rotational movement of said externally threaded control member relative to said pusher member; and (n) an administration set interconnected with said outlet of said fluid delivery member.

13. The apparatus as defined in claim 12 further including anti-rotation means carried by said container housing for preventing rotational movement of said externally threaded control member in a manner to move said pusher member from said second advanced position toward said first retracted position.

14. The apparatus as defined in claim 12 in which said pusher member is provided with a radial bore, in which said control member is provided with a radial bore in alignment with said radial bore of said pusher member and in which said locking means comprises a locking pin removably carried within said radial bores of said pusher member and said control member.

15. The apparatus as defined in claim 12 in which said chemical component is selected from a group consisting of: aluminum oxide, copper oxide, silicon elastomers, polybutadiene rubbers, bisphenol-A, iron oxide, aluminum, copper, phosphoric acid, iron, calcium, potassium, strontium oxide, sodium hydroxide, calcium chloride, magnesium chloride, iron chloride, zinc sulfate, copper sulfate, iron sulfate, sodium sulfate, barium iodide, calcium iodate, ammonium salts, sodium bicarbonate, potassium salts, acetone and pentane.

* * * * *